United States Patent [19]

Meserol et al.

[11] Patent Number: 4,902,629
[45] Date of Patent: Feb. 20, 1990

[54] APPARATUS AND PROCESSES FOR FACILITATING REACTION BETWEEN ANALYTE AND TEST REAGENT SYSTEM

[75] Inventors: Peter M. Meserol, Montville; Philip Bernstein, Glen Ridge; Rita C. Prodell, West Orange; Thomas Palmieri, Paramus, all of N.J.

[73] Assignee: Personal Diagnostics, Inc., Whippany, N.J.

[21] Appl. No.: 106,573

[22] Filed: Oct. 6, 1987

[51] Int. Cl.⁴ .............................................. G01N 31/22
[52] U.S. Cl. ...................................... 436/165; 422/58; 422/61; 422/68; 422/100; 435/805; 436/164
[58] Field of Search ...................... 422/55, 58, 61, 68, 422/100; 436/164, 165; 435/805

[56] References Cited

U.S. PATENT DOCUMENTS 4,058,146 11/1977 Citrin ............................... 422/100 X
4,088,448  5/1978 Lilja et al. ............................ 422/102
4,585,623  4/1986 Chandler ............................ 422/58 X
4,596,695  6/1986 Cottingham .................... 422/102 X

*Primary Examiner*—Barry S. Richman
*Assistant Examiner*—Jill Johnston
*Attorney, Agent, or Firm*—R. Gale Rhodes, Jr.

[57] ABSTRACT

Apparatus for and process of facilitating reaction between analyte contained in a sample and test reagent system at least one of which sample and test reagent system is a liquid, wherein the liquid one of the sample and test reagent system is placed in a reservoir, the other of the analyte and test reagent system is placed in capillary means dimensioned for entry into the reservoir, the reservoir and capillary means being mounted for at least relative movement towards each other and entry of the capillary means into the reservoir to draw by capillary attraction the liquid one of the sample and test reagent system from the reservoir into the capillary means and to bring the analyte and test reagent system into contact in the capillary means and facilitate the reaction.

61 Claims, 8 Drawing Sheets

TIME 0

TIME 1

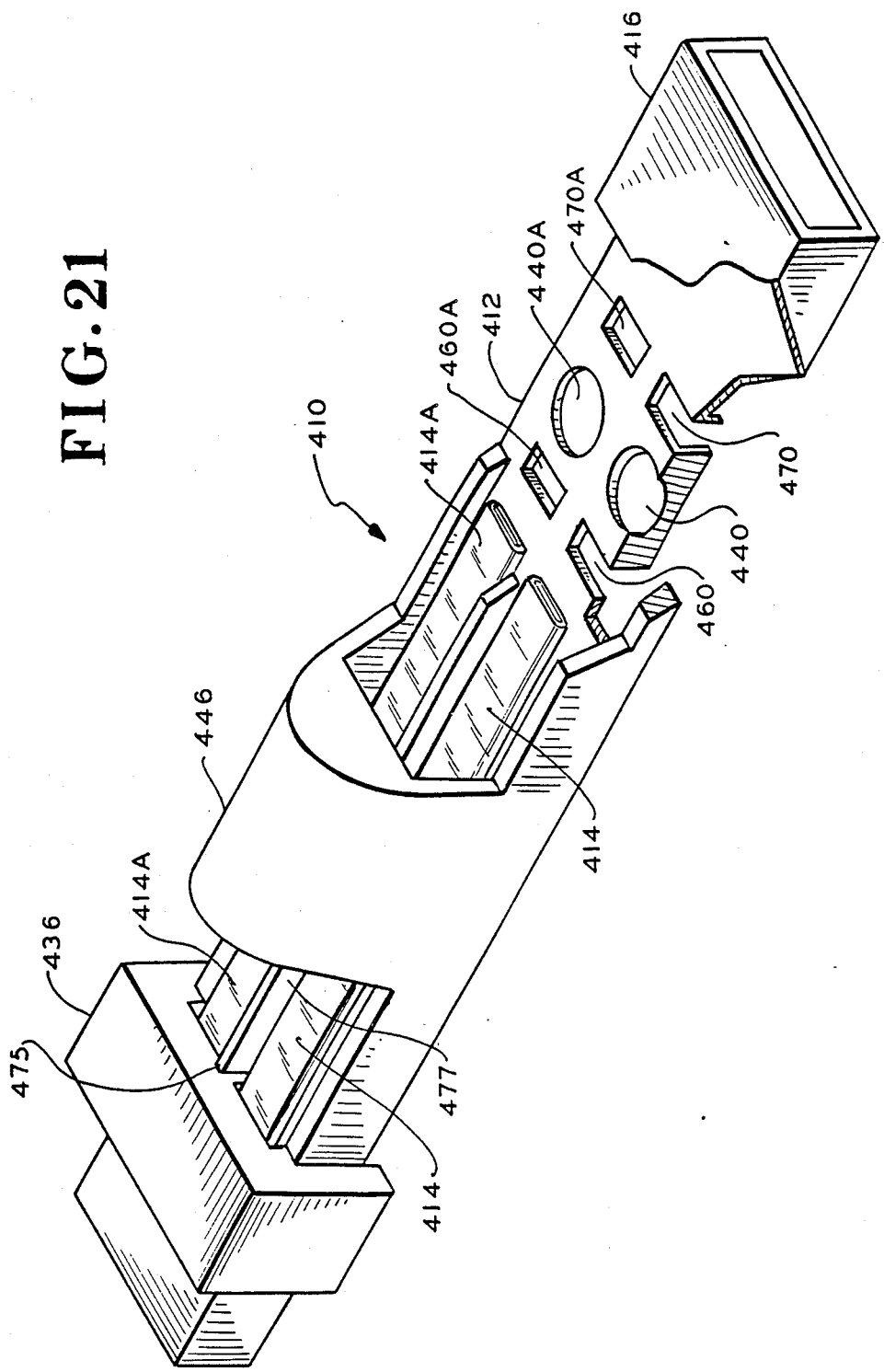

APPARATUS AND PROCESSES FOR FACILITATING REACTION BETWEEN ANALYTE AND TEST REAGENT SYSTEM

BACKGROUND OF THE INVENTION

This invention relates generally to new and improved apparatus and processes for facilitating reaction between analyte contained in a sample and test reagent system, and more particularly relates to new and improved apparatus and processes for enhancing facilitation of reaction between analyte contained in a sample and test reagent system wherein flow produced by capillary attraction, particularly turbulent flow, is utilized to bring a liquid one of sample and test reagent system into contact, particularly turbulent contact, with the other of the sample and test regent system to enhance facilitation of the reaction.

It will be understood that the term "analyte" is used in the specification and the appended claims to define something which is being analyzed, or determined, i.e. determined as to its presence or absence or presence to a significant extent, on the basis of whether or not a reaction, or a significant reaction, occurs with a test reagent system. Further, it will be understood that the term "test reagent system" as used in the specification and appended claims is used to define a system which has been adapted to react with the analyte upon its presence or presence to a significant extent. Analyte is typically contained in a sample, usually a liquid sample, for example the sample may be blood and the blood may be analyzed or a determination made with regard thereto as to whether or not antibodies to the human immunodeficiency virus (HIV) are present in the blood such antibodies being the analyte. The test reagent system may be latex beads coated with a certain human immunodeficiency virus (HIV) antigen, upon the antibodies being present and brought into contact with the antigen, an agglutination reaction occurs indicating a positive analysis or determination; thus it will be understood further that in the context of the present invention the analyte may be an antibody reagent and the test reagent system may be an antigen reagent, or vice versa. By way of further example, the analyte may be glucose contained in blood or blood serum, the test reagent system may be the Trinder reagent system, a colorimetric test reagent system, and upon the analyte being brought into contact with the Trinder test reagent system, and glucose analyte being present in the blood or blood serum sample, a change in color occurs to indicate, or provide the determination that, glucose is present in the sample. Other examples of analyte contained in a sample, e.g. liquid sample, are penicillin contained in milk, amylase contained in saliva, sodium chloride contained in sweat, bacteria contained in carrot juice; in each of these instances, a suitable test reagent system, e.g. a liquid test reagent system, would be provided to react with the analyte upon the analyte being present at least to a significant extent.

Analyte determination or analysis has been advanced by innumerable technological advances, yet many of the analyte determinations performed today require handling of sample containing the analyte and/or test reagent system; the use of ancillary equipment such as timers, test reagent system and/or sample containers or cuvettes; mixing devices (e.g. centrifuges, rotary mixers, mixing coils, pump, etc.) and reading devices (e.g. scanners, photometers, etc.). Additionally, the amounts of sample containing analyte/test reagent system required for testing may be large thereby increasing the cost per test to the point where they are at least undesirably high if not prohibitive for a large group of the present population.

Slide tests, and slide test apparatus are well known to those skilled in the analyte determination or analysis art, yet to perform a slide test requires the addition and mixing of the sample containing analyte and test reagent system for a prescribed time period whereafter the reaction, or test result, is then interpreted by direct visual observation or by an automatic optical reader. Typical slide test apparatus and processes are disclosed in U.S. Pat. No. 4,022,521 to Hall et al. patented May 10, 1977, U.S. Pat. No. 4,088,448 to Lilja et al. patented May 9, 1978, U.S. Pat. No. 4,171,866 to Tolles patented Oct. 28, 1979, and U.S. Pat. No. 4,596,695 to Cottingham patented Jun. 24, 1986. While the slide test apparatus and process disclosed in such prior art United States Patents may work well for their intended purposes, it has been found that there exists a present need for new and improved reaction apparatus and processes wherein, for example, the reaction time between the analyte and test reagent system is shortened (this is particularly important in presently needed large scale testing such as for the presence of the antibody to HIV in blood), facilitation of reaction between the analyte and test reagent system enhanced such as by increasing the number of reaction sites available therebetween (this is particularly important in those instances where for reason of cost, efficiency and timesaving it is desirable to use minimal amounts of analyte and test reagent system while retaining analyte determination sensitivity——this is especially important if the cost of the test reagent system is high or the amounts available for use are limited), and optical determination of the reaction enhanced.

By way of further background of the present invention, it will be understood that the term "optical determination" as used in the specification and the appended claims means determination of the presence or absence of a reaction between analyte and test reagent system, for example by the human eye, a beam of light such as used in a turbidimeter, and the like. By way of still further background, and as taught in detail below, the apparatus and processes of the present invention utilize "capillary means" and that "capillary means" is used in the specification and the appended claims to include a capillary tube having a small bore, or other structure such as a relatively large body of material having a small bore, into which bore a liquid may be elevated or drawn by capillary attraction. Still further, it will be understood that the term "liquid" as used in the specification and the appended claims means a liquid or other medium capable of being elevated or drawn into capillary means by capillary attraction. Still further it will be understood that the term "turbulent flow" as used in the specification and the appended claims is used to define fluid, e.g. liquid flow, in which the velocity at a given point changes constantly in magnitude and direction——contrasted with laminar flow; the term "turbulent flow" is further defined hereinbelow in the Description of the Invention and further contrasted with laminar flow.

SUMMARY OF THE INVENTION

The primary object of the present invention is to satisfy the foregoing needs which are satisfied by apparatus and processes of the present invention wherein reaction between analyte contained in a sample and test reagent system, at least one of which is a liquid, is facilitated by placing the liquid one of the sample and test reagent system in a reservoir, placing the other of the sample and test reagent system in capillary means, e.g. a capillary tube, dimensioned for entry into the reservoir, mounting the reservoir and capillary means for at least relative movement towards each other and entry of the capillary means into the reservoir, and providing relative movement towards each other and entry of the capillary means into the reservoir to draw by capillary attraction the liquid one of the sample and test reagent system from the reservoir into the capillary means and to bring the analyte and test reagent system into contact in the capillary means and facilitate the reaction.

DESCRIPTION OF THE DRAWINGS

FIG. 21 is a perspective view, partially in cross-section, of yet another embodiment of apparatus embodying the present invention and particularly useful for practicing processes of the present invention.

DESCRIPTION OF THE INVENTION

Figure 1:
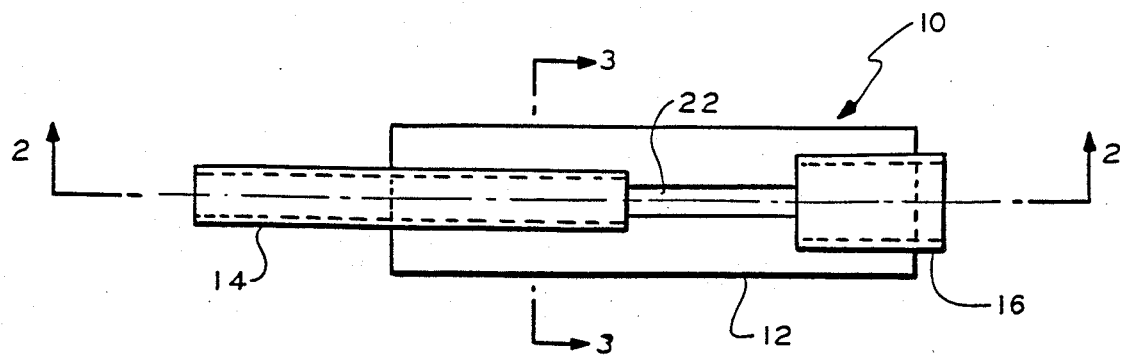
FIG. 1 is a top or plan view of apparatus embodying the present invention, which apparatus is particularly useful for practicing the process of the present invention.
Figure 2:
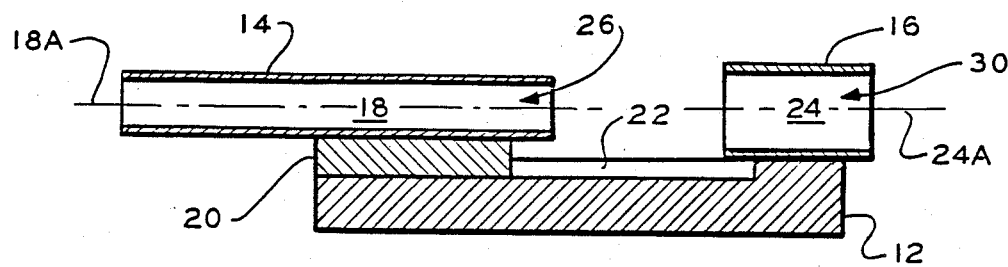
FIG. 2 is a sectional view taken generally along the line 2—2 in FIG. 1 in the direction of the arrows.
Figure 3:
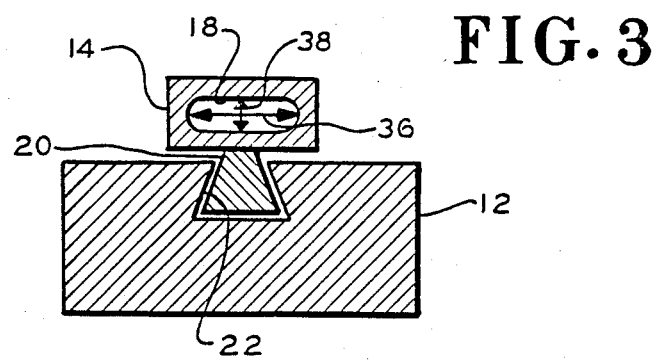
FIG. 3 is a cross-sectional view, enlarged, and taken generally along the line 3—3 in FIG. 1 in the direction of the arrows.

Referring now to FIGS. 1-3, there is illustrated apparatus for facilitating reaction between analyte contained in a sample and test reagent system embodying the present invention and identified by general numerical designation 10; apparatus 10 is particularly useful for practicing the processes of the present invention. Apparatus 10 may include a base or mounting member 12, a capillary tube 14 mounted slidably on the mounting member 12, and a reservoir 16 provided stationarily on the mounting member. The capillary tube 14 is provided with a bore 18 and the bottom of the capillary tube 14 may be secured, such as by a suitable adhesive, to a slide member 20 received slidably within a groove 22 formed in the mounting member 12, as may be seen best in FIG. 3, slide member 20 and groove 22 may be provided with complementary, cross-sectional shapes to assist maintaining the slide member in the groove. The reservoir 16 may be embodied as illustrated in FIGS. 1 and 2 as a capillary tube having a bore 24 and the reservoir 16 may be formed integrally with the mounting member 12 or formed separately and secured thereto in the position shown by a suitable adhesive. It will be understood that the capillary tube 14 is dimensioned, i.e. provided with a cross-sectional size and shape, permitting entry of the capillary tube 14 into the bore 24 of the reservoir 16. It still further will be understood that the capillary tube bore 18 has an axis 18A, that the reservoir bore 24 has an axis 24A, that the capillary tube 14 and reservoir 16 are mounted coaxially in opposed, spaced apart, end-to-end relationship, and that the capillary tube 14 is mounted slidably on the mounting member 12 through slide member 20, for movement towards and entry of at least the forward end thereof into the bore 24 of the reservoir 16.

Referring again to FIG. 2, and in accordance with the further teachings of the present invention, it will be understood that a liquid sample 26 (indicated by arrow 26) containing an analyte may be placed in the capillary tube 14 by pipetting, similarly, liquid test reagent system 30 (indicated by arrow 30) may be placed in the reservoir or capillary tube 16 by pipetting; alternatively, the sample 26 and liquid test reagent system 30 may be placed in the capillary tube and reservoir by a dropper, or the like. Thereafter, and in accordance with the further teachings of the present invention, and referring particularly to FIG. 4, the capillary tube 14 having the liquid sample 26 placed therein may be advanced by the fingers of an operator, in the direction of the arrow 34, towards the reservoir 16 sufficiently far to cause entry of the forward end of the capillary tube 14 into the reservoir 16 sufficiently far to cause the forward end of the capillary tube to engage at least the meniscus of the liquid test reagent system 30 residing in the bore 24 of the reservoir 16. Whereupon, and in accordance with the further teachings of the present invention, the liquid test reagent system 30 is drawn by capillary attraction from the reservoir 16 into the bore 18 of the capillary tube 14 to bring the liquid test reagent system 30 into contact with the analyte contained in the sample 26 in the bore 18 of the capillary tube 14 and facilitate reaction therebetween. The capillary tube 14 may be glass and, in accordance with the further teachings of the present invention, may be provided with a non-circular, cross-section, particularly having a flat top portion, as illustrated in FIG. 3 whereby optical determination, especially visualization by the human eye, may be enhanced or facilitated.

It will be under still further that in the preferred embodiment of the present invention, and in accordance with the further teachings thereof, the bore 18 of the capillary tube 14, FIG. 3, may be provided with a non-circular, cross-section having mutually perpendicular major and minor axes 36 and 38 wherein, in the preferred embodiment, the major-to-minor axis ratio is approximately 10:1. It has been discovered that such bore having a non-circular, cross-section provides turbulent flow by capillary attraction to the liquid test reagent system residing in the bore 24 of the reservoir 16 to draw the liquid test reagent system 30 from the reservoir 16 into the bore 18 of the capillary tube 14 with turbulent flow and to bring the liquid test reagent system 30 into turbulent contact with the analyte contained in the sample 26 residing in the bore 18 and enhance facilitation of reaction therebetween by, for example, increasing the number of reaction sites available between the analyte and test reagent system due to the turbulent contact therebetween.

Figure 5:
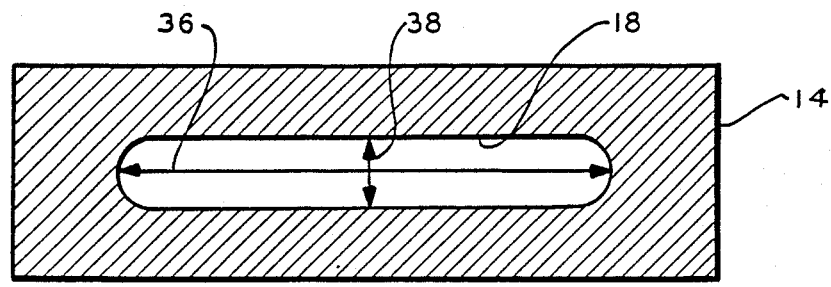
FIGS. 5, 6 and 7 are, respectively, enlarged cross-sectional views illustrating various embodiments of the bore configuration of capillary means embodying the present invention and particularly useful for providing turbulent flow to a liquid by capillary attraction.
Figure 6:
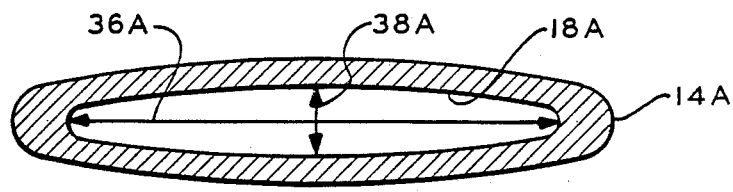
Figure 7:
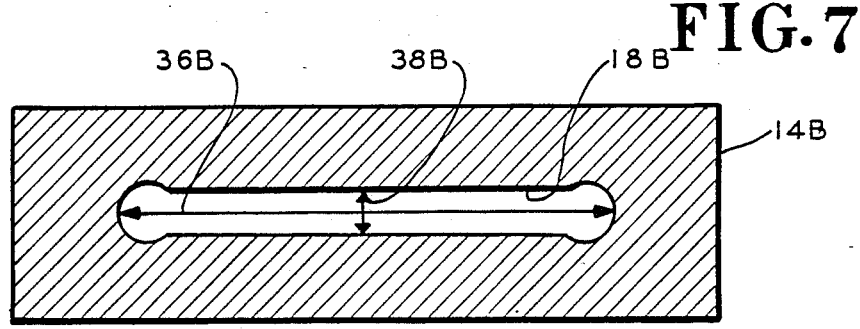

In alternate embodiments of the capillary tube 14 illustrated in FIGS. 5-7, the bore 18 (FIG. 5) may be defined by opposed flat surfaces interconnected by opposed generally circular, outwardly extending surfaces as shown having major and minor axes 36 and 38 of the ratio noted above. Alternatively as illustrated in FIG. 6, the capillary tube 14A may be provided with an oval, cross-sectional shape providing a bore 18A of oval, cross-sectional shape having major and minor axes 36A and 38A of the ratio noted above. Still further, alternatively, as illustrated in FIG. 7, the capillary tube 14B may be provided with a bore 18B having a non-circular, cross-sectional shape which is generally lemniscate (i.e. in the shape of a figure eight ("8") and more particularly an open figure eight ("8")) as shown and also having major and minor axes 36B and 38B of the above-noted major-to-minor axis ratio.

Figure 8:
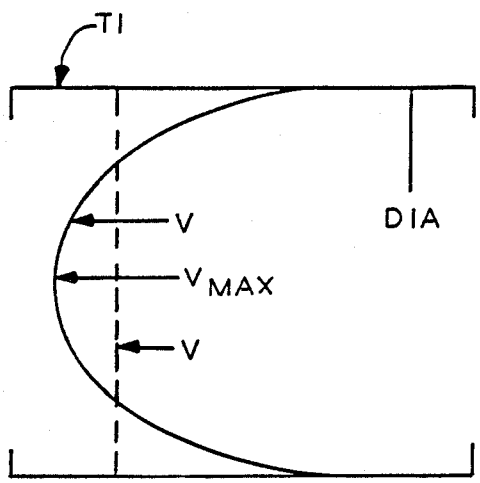
FIG. 8 is a diagrammatical illustration of laminar liquid flow.
Figure 11:
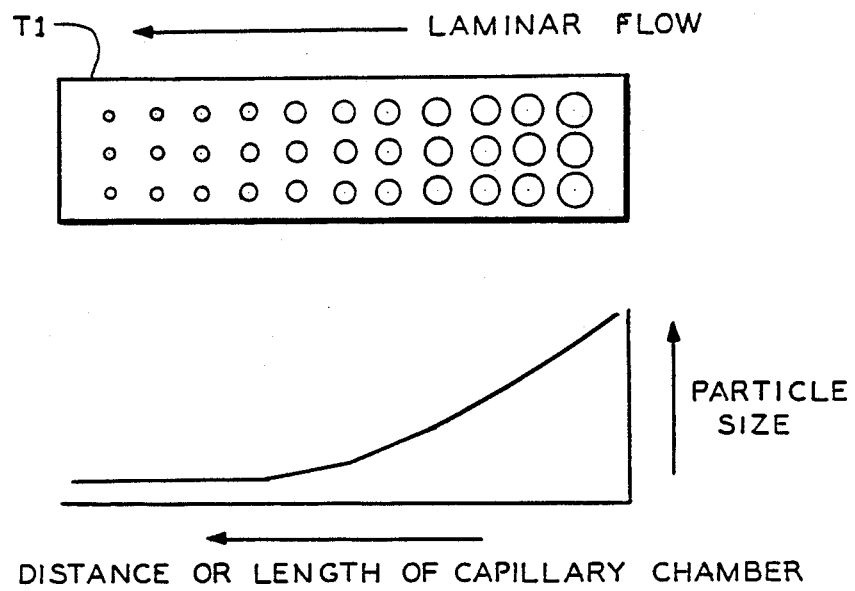
FIG. 11 is a composite diagrammatical illustration of agglutinated particle distribution provided with a gradient produced by laminar capillary flow.

A background of the fundamental difference between laminar liquid flow through a circular capillary tube and turbulent liquid flow through a capillary tube will now be provided so that a better understanding may be had of the advantages of the present invention, wherein turbulent liquid flow produced by capillary attraction is utilized to facilitate reaction between the analyte and test reagent system, over the prior art, particularly the above-noted slide test apparatus, wherein laminar liquid flow produced by capillary attraction is utilized to facilitate reaction between analyte and test reagent system. Referring to FIG. 8, a longitudinal section through circular capillary tubing T1 and a a laminar liquid flow pattern is illustrated; the parabola shown is the envelope of liquid flow velocity vectors with the velocity at the tubing wall being zero. At low flow rates, the movement of liquid through straight tubes of circular cross-section has a completely orderly flow pattern; the velocity at all points is parallel to the tube axis, there is no radial mixing except for molecular diffusion, and the velocity at a point is unchanging with respect to time. This flow is called laminar or Poiseuille flow. It is this type of flow, laminar flow, that is found in the above-noted prior art slide test apparatus particularly that shown in U.S. Pat. No. 4,596,695 to Cottingham identified above. Such laminar flow produces, in an agglutination reaction, an agglutinated particle size gradient or distribution as shown in FIG. 11 which is substantially the same as that illustrated in FIGS. 2C and 3C of the Cottingham patent wherein it will be noted that except for the initial agglutination reaction area at the beginning of the capillary chamber, the agglutinated particles are the largest at the forward end of the capillary chamber decreasing progressively in size to the rearward end of the chamber in the direction of laminar liquid flow. Thus, it will be understood that in the Cottingham patent the reaction particles are brought into contact in the capillary chamber with capillary attraction driven laminar flow generating a contact gradient between the reaction particles which decrease in the direction of laminar flow indicated by the arrow in FIG. 11.

Figure 9:
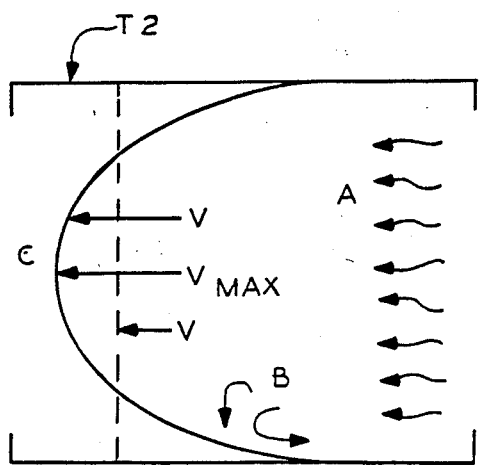
FIG. 9 is a diagrammatical illustration of turbulent fluid flow.

Referring now to FIG. 9, there is illustrated a longitudinal section through circular tubing T2 showing a turbulent flow pattern, A shows flow not always parallel to the tube axis, $\beta$ shows the shedding of an eddy, a type of turbulence, into the flow from behind a rough spot on the wall, C shows the time-averaged velocity profile, which has been flattened compared to the laminar liquid flow profile shown in FIG. 8. As the flow rate increases, the orderly flow pattern changes into chaotic motion, there is radial mixing, and the velocity at a point fluctuates due to inherent instabilities; this is called turbulent flow. Velocity at the wall of the tubing T2 is zero, as in laminar flow, but the parabolic velocity profile is flattened into a logarithmic one. Turbulent flow has more friction than laminar flow, and flow becomes turbulent when inertial forces (that perpetuate flow instabilities) dominate viscous forces (that dampen instabilities). The Reynolds number is a dimensionless ratio of these forces.

$$R_e = \varsigma VD/\mu = \text{inertial/viscous}$$

where $R_e$ represents the Reynolds number; $\varsigma$ represents density in g cm$^{-3}$; V represents average linear velocity in cm sec$^{-1}$; D represents diameter in cm; and $\mu$ represents dynamic viscosity in g cm$^{-1}$sec$^{-1}$ = poise. Turbulence usually starts when the Reynolds number reaches the 2000 to 4000 range. Increasing any of the above three variables in the numerator promotes turbulence.

Figure 10:
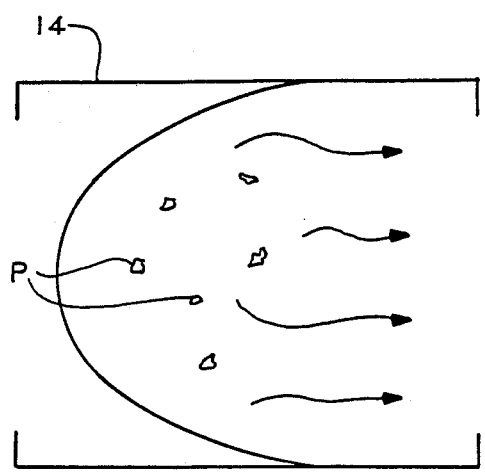
FIG. 10 is a diagrammatic illustration of turbulent flow enhanced by particle agglutination formation.
Figure 13:
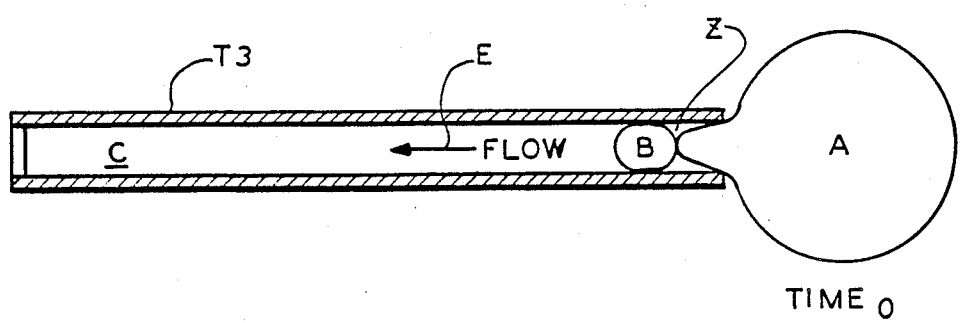
FIGS. 13 and 14 are diagrammatical illustrations in connection with a longitudinal-sectional view of a capillary tube illustrating capillary attraction driven turbulence contact gradient.
Figure 14:
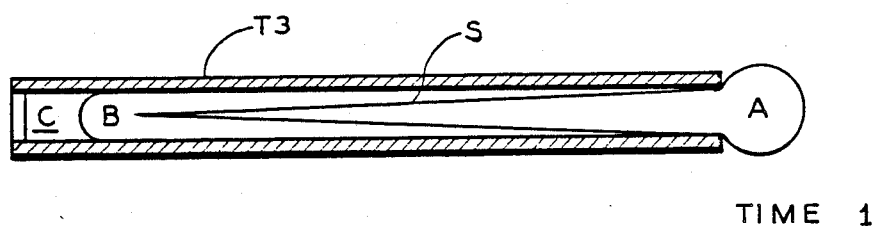

Applicant, as noted above, has discovered that this type of turbulent flow may be used to enhance reaction between analyte and test reagent system by bringing, for example with regard to FIGS. 1-7, the liquid test reagent system 30 into turbulent contact with the analyte contained in sample 26 by providing turbulent flow by capillary attraction to the liquid test reagent system 30 due to the non-circular, cross-section provided to the bore of the capillary tube 14 or 14A-14B illustrated in FIGS. 5-7. Further, and referring to FIG. 12, it has been discovered that such turbulent flow upon being provided to the liquid test reagent system 30 being drawn into the capillary tube 14, brings the analyte contained in the sample 26 and test reagent system 30 into capillary attraction driven turbulence generating a contact gradient therebetween, as shown in the bottom portion of FIG. 12, which gradient increases in the direction of turbulent flow as indicated by the arrow. While not wishing to be bound by theory, it is believed that it is this capillary attraction driven turbulence generating the contact gradient increasing in the direction of turbulent flow that causes an agglutination reaction, by rapid intermixing of analyte and test reagent system the reaction facilitated by the apparatus and process of the present invention to be completed in a much shorter length of time than the laminar flow utilized in the above-noted slide test prior art apparatus and process typified by the above-noted Cottingham patent. The benefits of such capillary attraction driven turbulence contacts gradient (FIG. 12) are illustrated diagrammatically in FIGS. 13 and 14. It is believed that maximum contact of reactants, i.e. analyte and test reagent system, occurs at the interface of the reactants identified as A and B at their interface Z which interface moves through the bore C of the capillary tube T3 under the driving force of capillary attraction and in the direction of turbulent fluid flow indicated by arrow E in FIG. 13. The reactants at time $T_o$ (FIG. 13), as separate boluses at contact, become a single column undergoing capillary driven contact and exchange as the capillary tube bore C fills (FIG. 14). The fluid velocity at the center of the moving fluid column is maximum with velocity at the bore wall being essentially zero. Thus, reactant A streams into reactant B. Given reactant B as a homogeneous dispersion of reactant particles, and reactant A as a fluid which causes those particles to clump or agglutinate together, it is believed that the streaming or telescoping of the reagents will cause the early formation of particles the flow characteristics of which enhance turbulence or vorticing in the fluid flow. This turbulence increases as the particles increase in size and are drawn along the capillary bore C under the influence of capillary attraction along with the moving reactant interfaces Z. FIG. 14, a time interval later ($T_1$), represents diagrammatically a formation of the intermixing gradient resulting from the capillary driven turbulent flow of reactant A into the capillary tube $T_3$ and mixing at the moving interface "Z" with reactant B. A long tapered stream S is characteristic of a gradient formation proportional to the concentrations found at points along the capillary bore C. As illustrated in FIG. 10, it is believed that the agglutinated particles P function similarly to B of FIG. 9 (rough spot in wall causing the eddy) and further enhance turbulent flow thereby further facilitating the reaction between the test reagent and the analyte.

Figure 4:
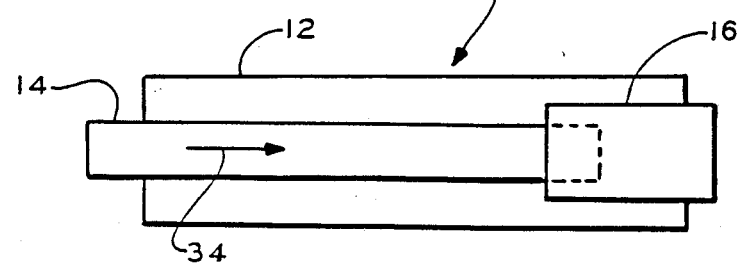
FIG. 4 is another plan view of the apparatus of FIG. 1 but showing the capillary means containing one of test reagent system and analyte advanced toward and having entered the reservoir containing the other of the test reagent system and analyte.
Figure 12:
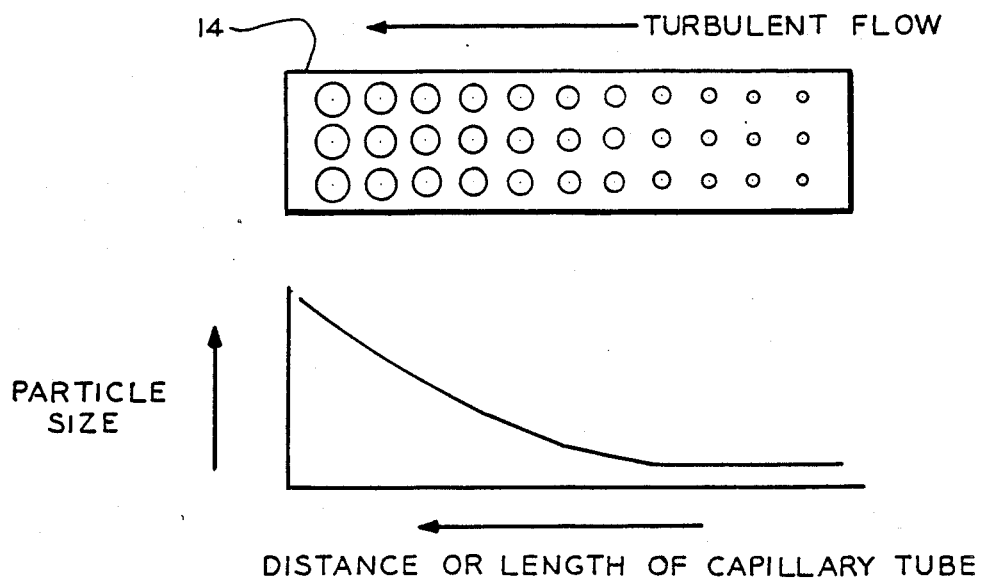
FIG. 12 is a composite diagrammatical illustration of agglutinated particle distribution provided with a gradient produced by turbulent capillary flow.

Apparatus embodying the present invention, and substantially the same as that illustrated in FIGS. 1-4, was utilized to determine the presence of AIDS antibody in blood serum. A latex test reagent system for AIDS antibody detection was used, the latex particles were 0.8μ in size and were coated with two glycoprotein fractions known to be detectable in the AIDS virus. Two μl of such latex liquid test reagent system were placed in the capillary tube 14 by capillary attraction. Thereafter, 20 μl of the analyte, i.e. blood serum known to contain antibodies to the AIDS virus (and thus antibodies to the two glycoproteins) were placed in the reservoir 16 by capillary attraction. Upon the capillary tube 14 being advanced into the reservoir 16, as illustrated in FIG. 4, the blood serum containing the AIDS antibody analyte was drawn into capillary tube 14 by capillary attraction with turbulent flow and brought into turbulent contact with the latex reagent system in the capillary tube 14; agglutination occurred very rapidly, in approximately 20 seconds, with the maximal or largest agglutinated particles being present at the distal end of the capillary tube 14 and with the agglutinated particles decreasing in size from the distal to the proximal end of the tube, evidencing that the analyte and test reagent system were brought into contact with capillary attraction driven turbulence generating a contact gradient therebetween increasing in the direction of turbulent flow as illustrated in FIG. 12. It will be understood that the sample 30 will be drawn into the bore 18 of the capillary tube 14 and the turbulence driven contact gradient between the analyte and test reagent system continued until the force of capillary attraction is exhausted.

Figure 15:
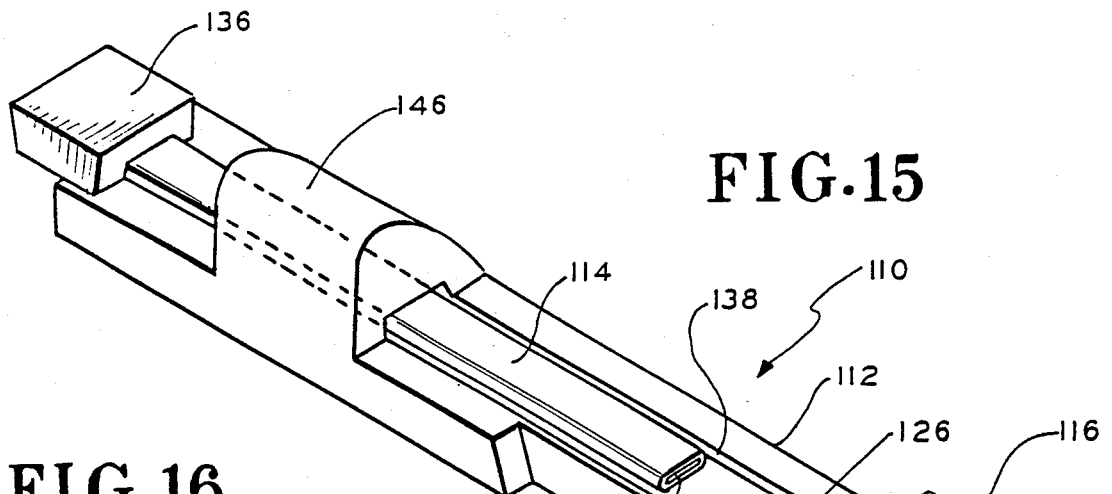
FIGS. 15, 16 and 17 are perspective views of apparatus embodying the present invention, particularly useful for practicing the processes of the present invention and illustrating the apparatus in three different stages of operation.
Figure 16:
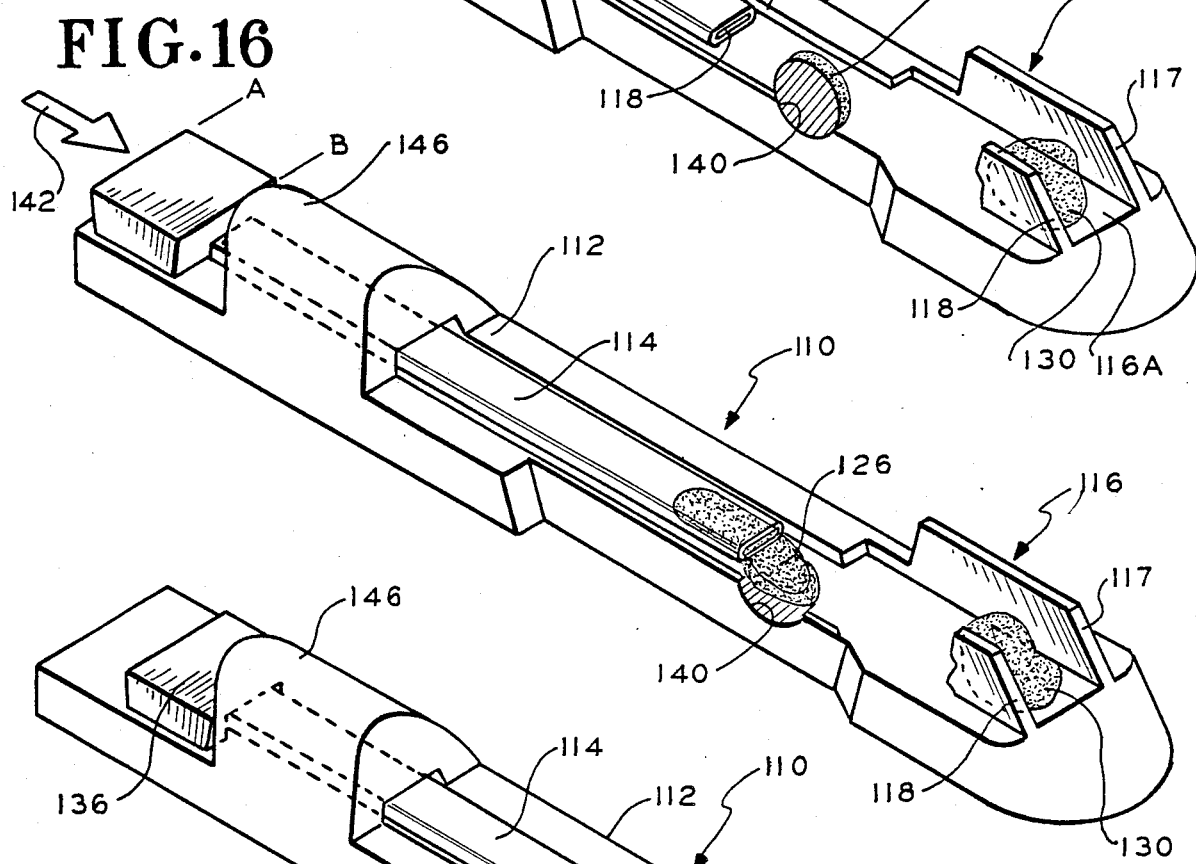
Figure 17:
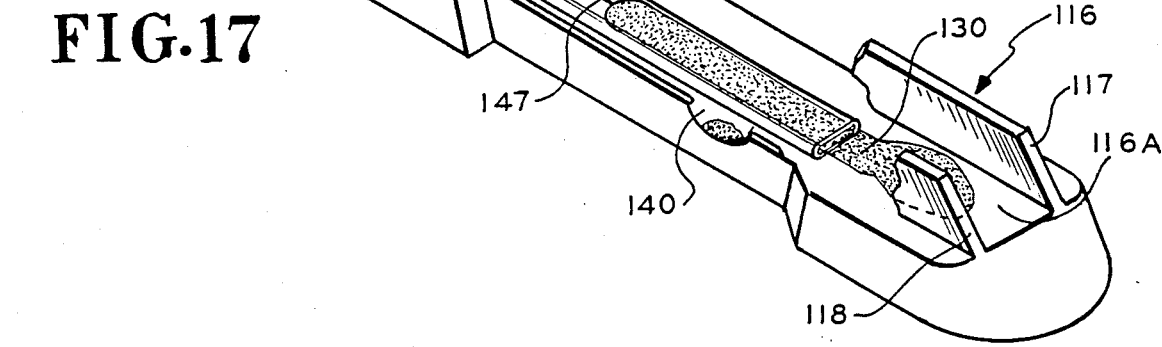

A further embodiment of the apparatus and process of the present invention is illustrated in FIGS. 15-17 with this apparatus embodiment being identified by general numerical designation 110. The apparatus includes a base or mounting member 112 on which is slidably mounted a capillary tube 114 and on which base is provided a reservoir indicated by general numerical designation 116; in this embodiment the reservoir is comprised of opposed, spaced apart, and upwardly extending members 117 and 118 providing the reservoir or reservoir space 116A therebetween. The capillary tube 114 is non-circular in cross-section and is provided with a bore 118 having a non-circular, cross-sectional shape which may be any one of those shown in FIGS. 7-9. The capillary tube 114 is secured at its rearward end to a manually operable slide or slide member 136, such as by being secured thereto by a suitable adhesive, and resides slidably in a groove or slot 138 provided in the top surface of the mounting member 112. Further, in this embodiment, the mounting member 112 is provided with a cavity or open chamber 140 which cavity, upon the capillary tube 114 being in the rearward position shown in FIG. 14, resides intermediate the opposed forward end of the capillary tube 114 and the reservoir 116.

In operation, in accordance with the process of the present invention, it will be understood that the cavity 140 may receive either the sample containing an analyte of interest or test reagent system, both of which are liquids in this embodiment, and the reservoir 116 may receive the other of the sample and test reagent system; for the purposes of this description, it will be presumed that the liquid test reagent system is placed in the cavity 140, such as by pipetting, and that the sample 130 is placed in the reservoir or reservoir space 116 also by pipetting. The slide member 136 will be gripped by the fingers of the operator and moved or advanced forwardly in the direction of the arrow 142 of FIG. 16 to slidably advance the capillary 114 forwardly in the slot 138 until the forward end thereof, as illustrated in FIG. 16, engages the liquid test reagent system 126 residing in the cavity 140 to cause the liquid test reagent system 126 to be drawn by capillary attraction into the bore 118 of the capillary tube 114 as shown. Thereafter, as illustrated in FIG. 17, the slide member 136 and capillary tube 114 are further advanced forwardly to cause the forward end of the capillary tube 114 to enter the reservoir 116 and engage at least the meniscus of the sample 130 residing in the reservoir to cause the sample 130 to be drawn into the bore 118 of the capillary tube 114 with turbulent flow by capillary action and into contact with the liquid test reagent system 126 residing in the capillary tube bore 118 to facilitate reaction between the analyte contained in the sample 130 and the test reagent system 126, it being understood, as taught above, that such turbulent flow and turbulent contact enhances facilitation of the reaction.

The capillary tube 114 may be made of glass, and the mounting member 112 may be made of a suitable plastic such as polystyrene and injection molded into the shape shown in FIGS. 15-17, the mounting member 112 may include a magnifying portion 146 enhancing optical determination of the reaction, it being understood that the turbulent flow provided by capillary attraction to the liquid test reagent system 126 and sample 130 advances them into the capillary tube 114 in the direction of the arrow 147 of FIG. 17 until the force of capillary attraction is exhausted, and it will be further understood that the magnifying portion 146 is provided on the mounting member 112 to reside in actual practice substantially over the area or length of reaction between the analyte and test reagent system within the bore 118 of the capillary tube 114.

Figure 18:
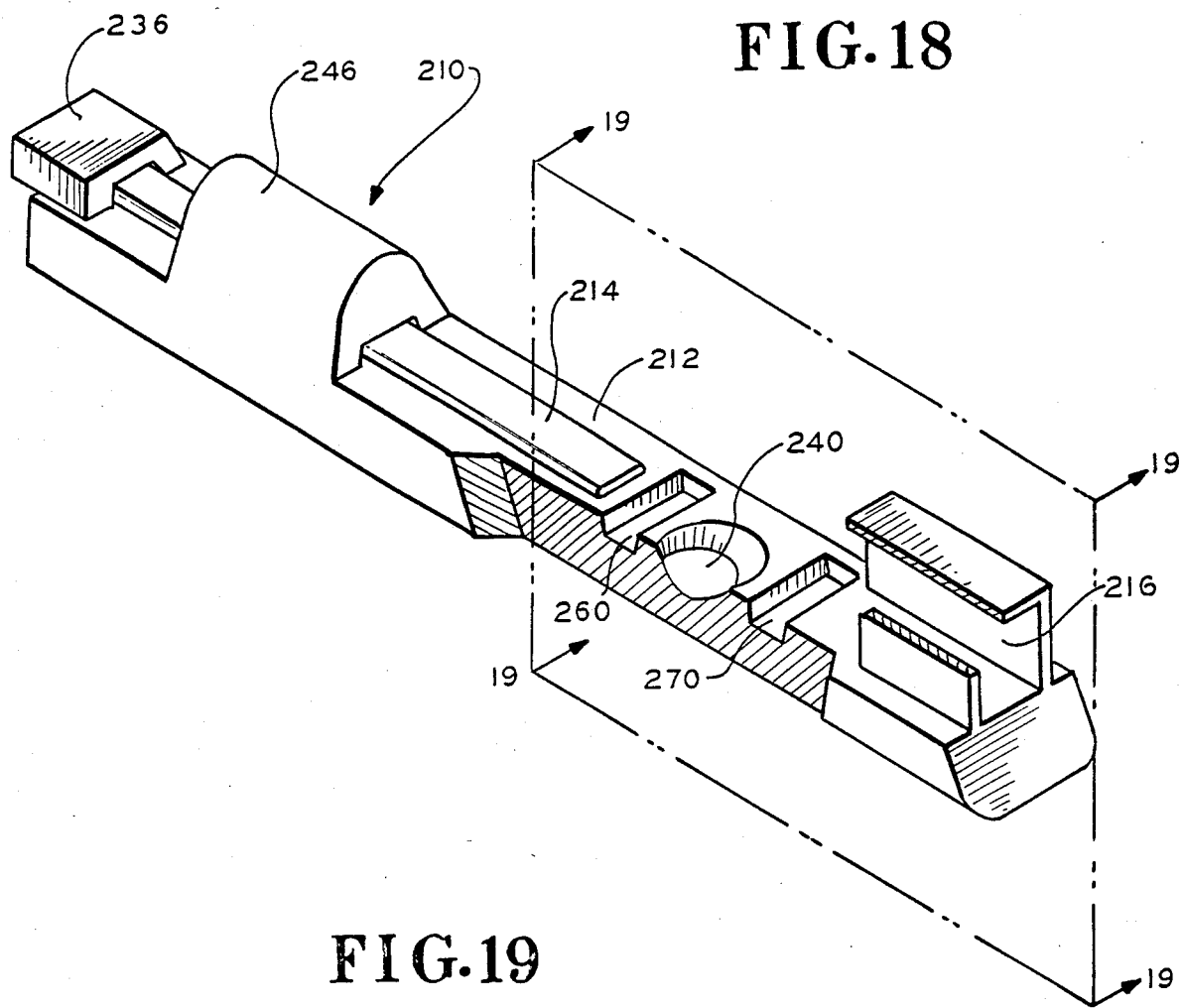
FIG. 18 is a perspective view, in partial cross-section, illustrating a further embodiment of apparatus embodying the present invention.
Figure 19:
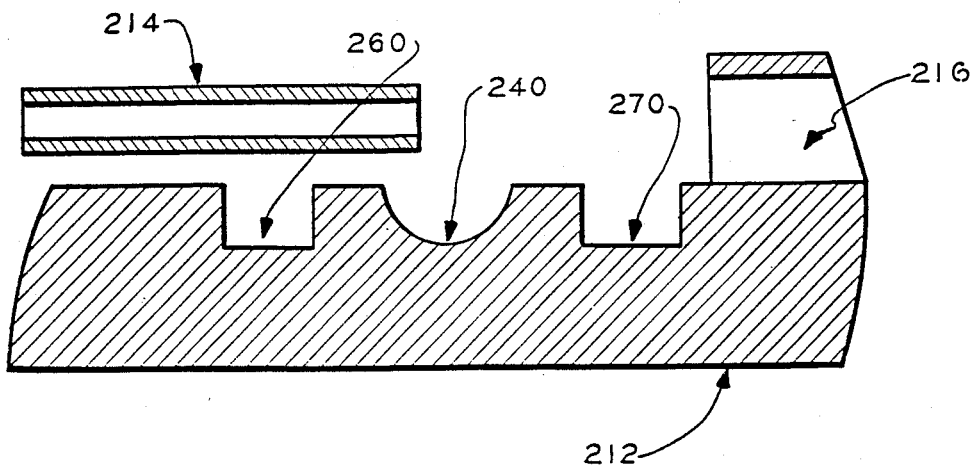
FIG. 19 is a cross-sectional view of a portion of the apparatus of FIG. 18 along the plane 19 in the direction of the arrows.

Referring now to FIGS. 18 and 19, a further embodiment of the present invention is illustrated which embodiment is substantially the same as that illustrated in FIGS. 15-17 except that in this embodiment the reservoir 216 is embodied as a capillary tube formed, such as by molding, integrally with the mounting member 212 and, except for the provision of the two cavities 260 and 270 shown disposed on either side of the cavity 240 for receiving either liquid sample containing an analyte of interest or liquid test reagent system. The cavity 260, upon the capillary tube 214 being in its rearward position as shown in FIG. 18, resides intermediate the forward end of the capillary tube 114 and the cavity 240 and prevents premature entry of either the liquid sample or liquid test reagent system residing in the cavity 240 and also prevents either the liquid analyte or liquid test reagent system residing in the cavity 240 from being drawn underneath the capillary tube 214 capillarity or wicking action; thus, it will be understood that the cavity 260 acts as a barrier for preventing such noted unwanted activity. The cavity 270 resides intermediate the cavity 240 and the reservoir 216 and provides a barrier for preventing either the liquid sample or liquid test reagent system residing in the cavity 240 from being drawn by capillary attraction into the reservoir 216.

Figure 20:
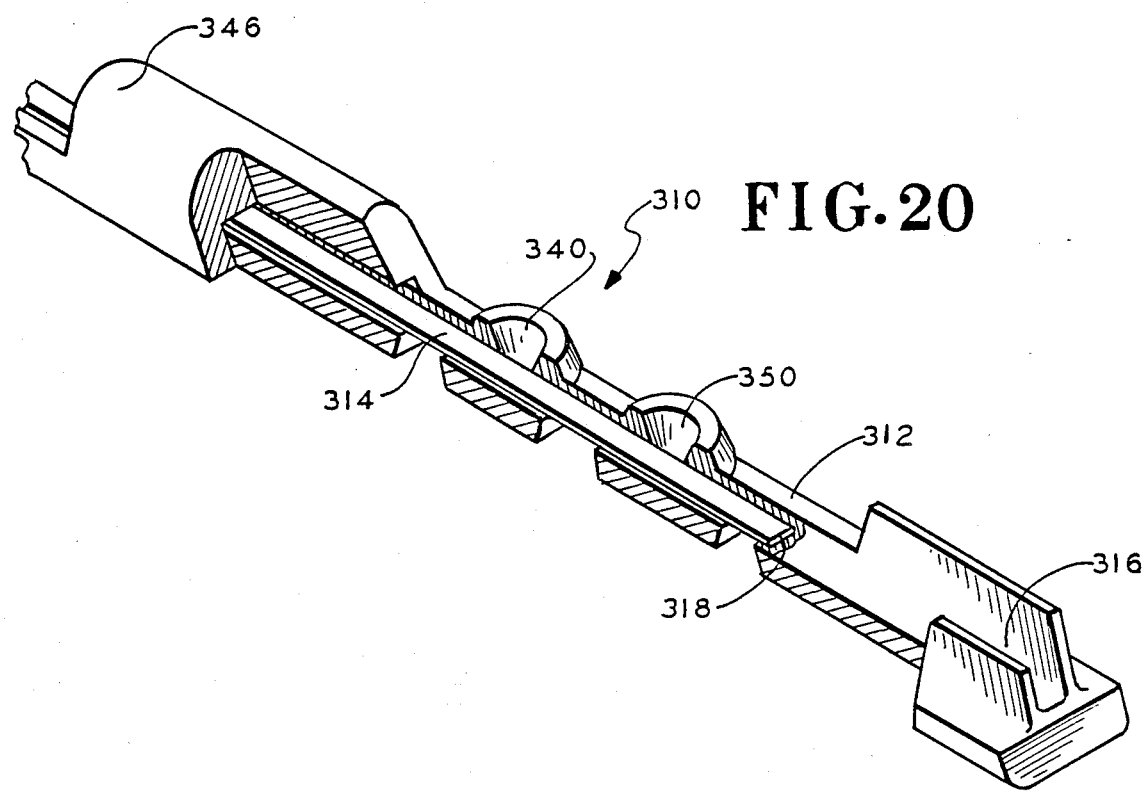
FIG. 20 is a perspective view, partially in a cross-section, of a still further embodiment of apparatus embodying the present invention, particularly useful for practicing processes of the present invention.

The apparatus and process alternate embodiments of the present invention illustrated in FIG. 20 have been found to be particularly useful for facilitating reaction between an analyte contained in a liquid sample and a first liquid test reagent system and for facilitating reaction between an admixture of the liquid sample and first liquid test reagent system and a second liquid test reagent system. The apparatus 310 of FIG. 20, it will be understood, is substantially similar to that of FIGS. 15-17 and FIGS. 18 and 19 and, accordingly, corresponding structure has been incremented by 100 in the numerical designations as may be noted. However, in the apparatus embodiment identified by general numerical designation 310, two cavities, 340 and 350, are provided on the mounting member 312 and, upon the capillary tube 314 being in its rearward position (not shown), the cavities 340 and 350 reside intermediate the forward end of the capillary tube 314 and the reservoir 316 and, as may be noted from FIG. 20, the capillary tube 314, cavities 340 and 350, and reservoir 316 are aligned linearly with the first cavity 340 adjacent the forward end of the capillary tube 314 and with the cavity 350 adjacent the reservoir 316. In this embodiment it will be noted that the capillary tube 314 is advanced through the cavities 340 and 350.

A better understanding of the apparatus of the alternate embodiment illustrated in FIG. 20, and the process practiced thereby, will now be presented by way of a description of the utilization of the apparatus 310 to determine whether or not a female is pregnant. The sample to be used is the fertile female's urine, and the analyte to be determined, whose presence usually indicates pregnancy and whose absence usually indicates non-pregnancy, will be hCG (human chorionic gonadotropin); hCG being, as is known, an antigen. The liquid urine sample may be placed in the cavity 340 by pipetting, a suitable liquid antibody reagent to hCG may be placed in the cavity 350 by pipetting, and a suitable liquid reagent containing latex beads coated with hCG antigen may be placed in the reservoir 316 by pipetting. The capillary tube 14, of course, will be at its rearward position (not shown in FIG. 20) and will be advanced forwardly to first cause the capillary tube to engage the liquid urine sample contained in cavity 340 to draw such sample by capillary attraction into the bore 318 of the capillary tube. Thereafter, the capillary tube will be further advanced into the cavity 315 to cause the liquid antibody reagent to hCG contained therein to be drawn into the capillary tube bore 318 by capillary attraction and to bring the hCG antigen analyte contained in the urine sample into turbulent contact with the antibody to hCG facilitating the above-noted reaction therebetween provided by the present invention which reaction will complex the hCG antibody and the analyte of the urine sample. Thereafter, the capillary tube will be advanced farther into the reservoir 316 to cause the liquid test reagent residing containing the latex beads coated with hCG to be drawn into the capillary tube bore 318 and since the antibody reagent contained in cavity 350 was complexed to the hCG antigen contained in the urine sample resulting in no antibody availability, agglutination will not occur and such absence of agglutination will be understood to indicate that the female is pregnant. Alternatively, it will be understood, were the female not to be pregnant, or her urine contain only a small amount of hCG, and her urine sample not to contain detectable hCG antigen, the antibody reagent to hCG contained in the cavity 350 would not be fully complexed upon entry into the capillary tube bore and contacting the urine and hence upon the liquid test reagent system containing latex beads with hCG antigen from the reservoir 316 being drawn into the capillary tube bore 318, the reaction facilitated by the present invention between such antibody and antigen will occur causing agglutination which presence will be understood to indicate that the female is not pregnant.

As is further known to those skilled in the art, it is often desirable, and in some instances required for validation, that a control test be performed concurrently, if not simultaneously, with the analytical reaction test to provide a basis of comparison for determining whether or not the analytical reaction test was an actual or true reaction or instead a false or spontaneous reaction. The further alternate apparatus 410 illustrated in FIG. 21, and the process practiced thereby, is particularly useful for contemporaneously facilitating an optically determinable reaction between an analyte of interest contained in a sample and an analytical or reaction test reagent system and a control test between the sample and a control or non-reactive test reagent system. It will be understood that the apparatus 410 of FIG. 21 is substantially similar, particularly, to that disclosed in FIGS. 18 and 19 and described above and, accordingly, corresponding structure in FIG. 21 has been incremented by 200 in the numerical designations vis-a-vis the corresponding structure illustrated in FIGS. 18 and 19. The primary difference between the apparatus 410 disclosed in FIG. 21 and the apparatus 210 disclosed in FIGS. 18 and 19 is that in addition to the capillary tube 414, cavity 440 and barrier cavities 460 and 470, there are provided a second capillary tube 414A, second cavity 440A and second barrier cavities 460A and 470A. As may be noted from FIG. 21, capillary tubes 414 and 414A are of the same length, disposed substantially parallel and secured to the slide member 436 for sliding advancement therewith and simultaneous entry of the forward ends of the capillary tubes 414 and 414A into the reservoir 416.

In operation, the reservoir 416 will be filled, either by capillary attraction or pipetting as taught above, with a sample containing an analyte of interest (e.g. the above-noted blood serum believed to contain antibodies to the AIDS virus) and an analytical or reactive liquid test reagent system (e.g. the above-noted liquid latex reagent system including latex beads or particles coated with two glycoprotein fractions known to be detectable in the AIDS virus) will be placed in the cavity 440, such as by pipetting, and a control or non-reactive liquid test reagent system (e.g. the above-noted liquid latex reagent system including latex beads or particles not coated with the two glycoprotein fractions known to be detectable in the AIDS virus) will be placed in the cavity 440A such as by pipetting. Upon advancement of the slide member 436, for example by force applied by the fingers of an operator, the capillary tubes 414 and 414A will be advanced to first engage, respectively, the analytical or reactive liquid test reagent system residing in cavity 440 and the control or non-reactive test reagent system residing in cavity 440A to cause such respective liquid test reagent systems to be drawn by capillary attraction into the capillary tubes 414 and 414A, whereafter upon continued advancement of the slide member 436 and the capillary tubes 414 and 414A the forward ends of the capillary tubes 414 and 414A will be advanced into the reservoir 416 to draw by capillary attraction respective portions of the sample contained therein into the respective capillary tubes. Whereafter, reaction between the analyte contained in the sample portion drawn into capillary tube 414 and the analytical or reactive liquid test reagent system will be facilitated, as taught hereinabove, and the sample portion drawn into capillary tube 414A will not react with the control or non-reactive liquid test reagent system. It will be understood further that the actual agglutination reaction occurring in capillary tube 414 may be viewed, or optically determined, through the magnifying portion 446 of the apparatus 410 and the absence of a reaction in the capillary tube 414A also may be viewed or optically determined through the magnifying portion 446, and thus a visual or optical comparison may be made to establish the validity of the reaction present in capillary tube 414.

It further will be understood by those skilled in the art that the capillary tubes 414 and 414A of apparatus 410 may each be provided with a bore having a non-circular, cross-section of the various embodiments taught hereinabove and disclosed in FIGS. 7-9 for the reasons and advantages also taught hereinabove and that the capillary tubes 414 and 414A may be made of glass facilitating optical determination of a reaction, or non-reaction, occurring therein.

Still further, and referring again to the apparatus 410 of FIG. 21, it will be noted that the slide member 436 may be provided with an inwardly extending groove 475 for receiving in sliding relationship the complementary shaped upwardly extending rib 477 formed on the mounting apparatus 412 to facilitate maintaining the slide member 436, and hence the capillary tubes 414 and 414A secured thereto, in coaxial alignment with the reservoir 416 particularly during advancement as described above.

Still further, it will be understood that the capillary tubes 414 and 414A may be of the same length as shown and described above or, if it is desired to begin either the control test or analytical or reactive test earlier than the other, either of the forward ends of the capillary tubes may be shortened with respect to the other to provide this displacement in time and commencing of the respective tests or reactions. Further, it will be understood that the reservoir 416 may be capillary means as shown in FIG. 21 or may be a reservoir provided, for example, by the upwardly extending members illustrated in FIGS. 15-17 providing the reservoir 116 or reservoir space 116A.

Referring again to apparatus 10 and the placing of the sample containing an analyte of interest in the reservoir 16 illustrated diagrammatically in FIG. 5, it will be understood that alternatively, for example, when the sample is blood containing an analyte of interest, the blood may be provided by a finger prick and the blood may be drawn off directly by capillary attraction by placing the rearward end of the reservoir 16 in contact with droplet of blood produced at the finger prick to a predetermined calibration mark which calibration mark may be provided on the reservoir 16.

It further will be understood, and in accordance with the further teachings of the present invention, that the various apparatus described above and shown in the drawings embodying the alternative embodiments of the present invention may attached to a card or other support by suitable means such as snap-in buttons or posts provided on the bottoms of the various mounting members. This permits backgrounds of different colors, textures and compositions provided on the card or support, e.g. the top surface thereof, to be employed. For a latex agglutination reaction, or agglutination inhibition reaction test, a dark or black background may be provided on such top surface to enhance optical determination, e.g. visualization by the human eyes, of the presence or absence of the reactions, and such may also be used when turbidimetric reactions are read enhancing reading by a beam of light. In contrast, a white background, or one of contrasting color to the reaction, may be provided on the top surface of the card or support to enhance optical determination, e.g. human visualization, of a colorimetric reaction test result, for example an enzyme reaction test or enzyme immunoassay reaction test including a chromophore.

It further will be understood by those skilled in the art that the apparatus and process of the present invention may be used in a variety of test reaction systems, for example the device is particularly useful for, but not limited to, reaction tests using particulate markers, agglutination or agglutination inhibition reaction tests, turbidimetric and nephelometric reaction tests, coagulation, colorimetric and enzyme or enzyme-mediated, luminescent, fluorometric, reaction tests.

Still further, it will be understood by those skilled in the art that the apparatus and process of the present invention are particularly useful for facilitating analytical reaction tests which require only minimal amounts of the sample and test reagent system, facilitate rapid reactions, provide for easy optical determination, e.g. human visualization, of the reaction results or absence thereof, provide a disposable test apparatus that requires minimal handling and which may be made sufficiently inexpensively that it may be a disposable, provides a non-labor intensive apparatus capable of being employed by individuals not trained in the performance of analytical tests, and provides, as noted above, apparatus wherein a variety of tests may be performed, viz. agglutination or agglutination inhibition, colorimetric, turbidimetric, enzyme mediated and immunoassays, etc..

Lastly, it will be understood by those skilled in the art that many variations and modifications may be made in the present invention without departing from the spirit and the scope thereof.

What is claimed is:

1. An apparatus for facilitating reaction between test reagent system and analyte contained in a sample, wherein one of said test reagent system and sample is a liquid and the other of said test reagent system and sample is either a liquid or a non-liquid, comprising:
   a first capillary tube provided with a first bore having a non-circular cross-section for receiving said other of said test reagent system and sample,
   reservoir means for receiving said one of said test reagent system and sample,
   said first capillary tube dimensioned for entry into said reservoir means and said first capillary tube and said reservoir means mounted for at least relative movement towards each other and entry of said first capillary tube into said reservoir means to draw by capillary attraction said one of said test reagent system and sample from said reservoir means into said bore and to bring said test reagent system and sample into turbulent contact in said bore and facilitate said reaction.

2. The apparatus according to claim 1 wherein said other of said test reagent system and sample is a liquid and wherein said capillary tube bore receives said other of said test reagent system and sample by capillary attraction.

3. The apparatus according to claim 2 wherein said bore is for providing turbulent flow by said capillary attraction to said one of said test reagent system and sample to bring said test reagent system and analyte into said turbulent contact in said bore of said first capillary tube and enhance facilitation of said reaction.

4. The apparatus according to claim 2 wherein said bore is for providing turbulent flow to said one of said test reagent system and sample by said capillary attraction and for bringing said test reagent system and analyte into contact in said first capillary tube with capillary attraction driven turbulence generating a contact gradient therebetween increasing in the direction of turbulent flow to enhance facilitation of said reaction.

5. The apparatus according to claim 1 wherein said reservoir means are second capillary means comprising a second capillary tube for receiving said one of said test reagent system and sample by capillary attraction.

6. The apparatus according to claim 1 wherein said reservoir means comprise opposed, spaced apart members providing a reservoir therebetween for receiving said one of said test reagent system and sample by pipetting.

7. The apparatus according to claim 1 wherein said first capillary tube has a first longitudinal axis, wherein said reservoir means comprises a second capillary tube having a second longitudinal axis, and wherein said apparatus includes mounting means for mounting said first and second capillary tubes in generally coaxial, opposing and spaced apart end-to-end relationship and wherein said first capillary tube is mounted slidably on said mounting means for at least sliding relative movement towards and entry into said second capillary tube.

8. The apparatus according to claim 7 wherein said other of said test regent system and sample is a liquid and wherein said mounting means is provided with a cavity which upon said first capillary tube being in a rearward position resides intermediate the opposed ends of said first capillary tube and said reservoir means, said cavity for receiving said other of said test reagent system and sample and wherein said slidably mounted first capillary tube upon said sliding relative movement from said rearward position towards said second capillary tube engages said other of said test reagent system and sample residing in said cavity to cause said other to be drawn by capillary attraction into said first capillary tube before entry thereof into said reservoir means.

9. The apparatus according to claim 8 wherein said mounting means are provided with second barrier means intermediate said cavity and said second capillary tube for preventing the other of said test reagent system and sample from being drawn into said second capillary tube by capillary attraction.

10. The apparatus according to claim 8 wherein said mounting means are provided with first barrier means which upon said first capillary tube being in said rearward position resides intermediate said first capillary tube and said cavity, said first barrier means for preventing premature entry of said other of said test reagent system and sample into said first capillary tube by capillary attraction.

11. The apparatus according to claim 10 or 9 wherein each of said barrier means comprise an additional cavity formed in said mounting means.

12. The apparatus according to claim 1 wherein said bore non-circular cross-section has mutually perpendicular major and minor axes having a major to minor axis ratio of approximately 10 to 1.

13. The apparatus according to claim 12 wherein said major axis is approximately 1000-2000 microns in length and wherein said minor axis is approximately 100-200 microns in length, with said 10:1 ratio being maintained.

14. The apparatus according to claim 1 wherein said bore is defined by opposed flat surfaces interconnected by opposed generally circular, outwardly extending surfaces.

15. The apparatus according to claim 1 wherein said bore non-circular cross-section is generally oval.

16. The apparatus according to claim 1 wherein said bore non-circular cross-section is generally lemniscate.

17. An apparatus for facilitating reaction between a first liquid test reagent system and analyte contained in a liquid sample, and for facilitating reaction between an admixture of said first liquid test reagent system and liquid sample and a second liquid test reagent system, comprising:
    mounting means;
    reservoir means provided on said mounting means, said reservoir means having an entrance and for receiving said second liquid test reagent system;
    capillary means mounted slidably on said mounting means and for advancement from a rearward position towards and entry into said reservoir means through said entrance thereof;
    first and second cavities provided in said mounting means and upon said capillary means being in said rearward position said cavities residing intermediate said capillary means and said reservoir means with said capillary means, cavities and reservoir means being aligned linearly with said first cavity adjacent said capillary means and with said second cavity adjacent said reservoir means;

said first cavity for receiving said liquid sample and said second cavity for receiving said first liquid test reagent system; and upon said capillary means being advanced from said rearward position towards said reservoir said capillary means engaging said liquid sample to draw said sample therein by capillary attraction, upon continued advancement of said capillary means said capillary means engaging said first liquid test reagent system to draw said first liquid test reagent system therein by capillary attraction to provide an admixture of said first liquid test reagent system and said sample and and to bring said analyte and said first liquid test reagent system into contact in said capillary means and facilitate said reaction therebetween, and upon further continued advancement of said capillary means said capillary means entering said reservoir means and engaging said second liquid test regent system to draw said second liquid test reagent therein by capillary attraction and to bring said second liquid test reagent system and said admixture into contact in said capillary means to facilitate said reaction therebetween.

18. The apparatus according to claim 1 or 17 wherein said capillary means is provided with at least an optically transparent portion enabling optical determination of said reaction.

19. The apparatus according to claim 7 or 17 wherein said capillary means comprises a capillary tube provided with at least an optically transparent portion enabling optical determination of said reaction and wherein said mounting means is provided with a magnifying portion for magnifying the view of said reaction in said capillary tube to enhance visual perception thereof by the human eye.

20. The apparatus according to claim 17 wherein said capillary means comprise a capillary tube provided with a bore having a non-circular cross-section for providing turbulent flow by said capillary attraction respectively to said first and second liquid test reagent systems to bring said systems into turbulent contact in said capillary means respectively with said sample an said admixture and enhance facilitation of said reactions.

21. The apparatus according to claim 17 wherein said capillary means is a capillary tube provided with a bore having a non-circular cross-section for providing turbulent flow to said first liquid test reagent system by said capillary attraction and for bringing said first liquid test reagent system into contact with said analyte in said capillary tube with capillary attraction driven turbulence generating a contact gradient therebetween increasing in the direction of turbulent flow to enhance facilitation of said reaction therebetween, and for providing turbulent flow to said second liquid test reagent system by said capillary attraction and for bringing said second liquid test reagent system into contact with said admixture of said sample and said first liquid test reagent system in said capillary tube with capillary attraction driven turbulence generating a contact gradient therebetween increasing in the direction of turbulent flow to enhance facilitation of said reaction therebetween.

22. The apparatus according to claim 17 wherein said reservoir means are second capillary means for receiving said second liquid test reagent system by capillary attraction.

23. The apparatus according to claim 17 wherein said reservoir means comprising opposed, spaced apart members providing a reservoir therebetween for receiving said second liquid test reagent system by pipetting.

24. An apparatus for facilitating reaction between analyte contained in a liquid sample and an analytical test reagent system, and for providing a control test between said sample and a control test reagent system for comparison with said reaction to determine the validity thereof, comprising:

first capillary means for receiving said analytical test reagent system;

second capillary means for receiving said control test reagent system;

reservoir means for receiving said liquid sample; and said first and second capillary means dimensioned for entry into said reservoir and said first and second capillary means and said reservoir means mounted for at least relative movement toward each other and entry of said first and second capillary means into said reservoir means to draw by capillary attraction respective portions of said sample into said first capillary means and said second capillary means to bring said analyte and analytical test reagent system into contact in said first capillary means and facilitate said reaction therebetween and to bring a portion of said sample and said control test reagent system into contact in said second capillary means to provide said control test.

25. The apparatus according to claim 24 wherein each of said first and second capillary means are each a capillary tube provided with a bore having a non-circular cross-section for providing turbulent flow by said capillary attraction to said portions of said liquid sample and to bring said analyte into turbulent contact with said analytical test reagent system in said first capillary tube and to bring a portion of said liquid sample into turbulent contact with said control test reagent system in said second capillary tube.

26. The apparatus according to claim 24 wherein each of said first and second capillary means are a capillary tube provided with a bore having a non-circular cross-section for providing turbulent flow to said portions of said sample by said capillary attraction and for bringing said analyte into contact with said analytical test reagent system in said first capillary means with capillary attraction driven turbulence generating a contact gradient therebetween increasing in the direction of turbulent flow to enhance facilitation of said reaction and for bringing a portion of said sample into contact with said control liquid test reagent system in said second capillary means with capillary attraction driven turbulence generating a contact gradient therebetween increasing in the direction of turbulent flow to enhance said control test.

27. The apparatus according to claim 24 wherein said analytical and control test reagent systems are each a liquid and wherein said first and second capillary means comprise first and second capillary tubes and wherein said analytical liquid test reagent system and said control liquid test reagent system are received, respectively, in said first and second capillary tubes by capillary attraction.

28. The apparatus according to claim 24 wherein said reservoir means are third capillary means for receiving said sample by capillary attraction.

29. The apparatus according to claim 24 wherein said reservoir means comprises opposed, spaced apart members providing a reservoir therebetween for receiving said analyte by pipetting.

30. The apparatus according to claim 24 wherein each of said first and second capillary means are provided with at least an optically transparent portion for enabling optical determination respectively of said reaction and said control test.

31. The apparatus according to claim 24 wherein said apparatus further comprises mounting means and a slide member mounted slidably on said mounting means for sliding advancement toward said reservoir means, wherein said reservoir means are provided on said mounting means, and wherein said first and second capillary means comprise first and second capillary tubes disposed substantially parallel and secured to said slide member for sliding advancement therewith and upon advancement of said slide member toward said reservoir means, said first and second capillary tubes are advanced concurrently into said reservoir means.

32. The apparatus according to claim 31 wherein said first and second capillary tubes are each provided with at least an optically transparent portion enabling optical determination respectively of said reaction and said control test, and wherein said mounting means is provided with a magnifying portion for magnifying the views of said reaction and control test to enhance visual perception and comparison thereof by the human eye.

33. In an apparatus for facilitating reaction between analyte contained in a sample and test reagent system, wherein at least one of said sample and test reagent system is a liquid
WHEREIN THE IMPROVEMENT COMPRISES:
means comprising a capillary tube including a bore of non-circular cross-section for providing turbulent flow to said liquid one of said sample and test reagent system and for flowing said liquid one into turbulent contact with the other of said sample and test reagent system to bring said analyte and test regent system into turbulent contact and enhance facilitation of said reaction.

34. In an apparatus for facilitating reaction between analyte contained in a sample and test regent system, wherein at least one of said sample and test regent system is a liquid
WHEREIN THE IMPROVEMENT COMPRISES:
means comprising a capillary tube including a bore of non-circular cross-section for providing turbulent flow to said liquid one of said sample and test reagent sample and bringing said analyte and test reagent system into contact with capillary attraction driven turbulence generating a contact gradient therebetween increasing in the direction of turbulent flow to enhance facilitation of said reaction.

35. A process of facilitating reaction between analyte contained in a sample and test reagent system, wherein at least one of said sample and test reagent system is a liquid, comprising the steps of:
placing said liquid one of said sample and test reagent system in reservoir means;
placing the other of said sample and test reagent system in a bore of non-circular cross-section provided in a capillary tube, said capillary tube dimensioned for entry into said reservoir means;
mounting said reservoir means and said capillary tube for at least relative movement towards each other and entry of said capillary tube into said reservoir means; and
providing said relative movement towards each other and entry of said capillary tube into said reservoir means to draw by capillary attraction said one of said sample and test reagent system from said reservoir means into said bore and to bring said analyte and test reagent system into turbulent contact in said bore and facilitate said reaction.

36. The process according to claim 35 including the further steps of drawing by said capillary attraction said one of said sample and test reagent system from said reservoir into said capillary tube with turbulent flow to bring said analyte and test reagent system into turbulent contact in said capillary tube and enhance facilitation of said reaction.

37. The process according to claim 36 including the further steps of providing turbulent flow to said one of said sample and test reagent system by said capillary attraction and bringing said analyte and test reagent system into contact in said capillary tube with capillary attraction driven turbulence generating a contact gradient therebetween increasing in the direction of turbulent flow to enhance facilitation of said reaction.

38. The process according to claim 35 wherein the other of said sample and test reagent system is a liquid and wherein said process includes the further step of placing said other of said sample and test reagent system in said capillary means by capillary attraction.

39. The process according to claim 35 wherein said reservoir means are capillary means and wherein said process includes the further step of placing said one of said sample and test reagent system in said reservoir means by capillary attraction.

40. The process according to claim 35 wherein said capillary tube has a first longitudinal axis, wherein said reservoir means is provided with a second longitudinal axis and wherein said mounting step comprises the step of mounting said capillary tube and said reservoir means in generally coaxial, opposing and spaced apart end-to-end relationship and mounting said capillary tube slidably on mounting means for at least sliding relative movement towards and entry into said reservoir means.

41. The process according to claim 40 wherein the other of said sample and test reagent system is a liquid and wherein said process includes the further step of providing a cavity for receiving said other of said sample and test reagent system and which cavity, upon said capillary tube being in a rearward position, resides intermediate the opposed ends of the capillary tube and said reservoir means and wherein the process includes the further step of advancing said capillary tube from said rearward position towards said reservoir means to engage said other of said sample and test reagent system residing in said cavity to cause said other of said sample and test reagent system to be drawn by capillary attraction into said capillary tube before entry thereof into said reservoir means.

42. The process according to claim 41 wherein said process includes the further step of providing a first barrier intermediate said capillary tube and said cavity to prevent premature entry of said other of said sample and test reagent system into said capillary tube by capillary attraction.

43. The process according to claim 42 wherein said process includes the further step of providing a second barrier intermediate said cavity and said reservoir means to prevent the other of said sample and test reagent system from being drawn into said reservoir means by capillary attraction.

44. A process of facilitating reaction between analyte contained in a liquid sample and a first liquid test reagent system and of facilitating reaction between an admixture of said sample and said first liquid test reagent system and a second liquid test reagent system, comprising the steps of:
placing said second liquid test reagent system in a reservoir provided with an entrance;
mounting capillary means slidably for advancement from a rearward position towards and entry into said reservoir through said entrance;
placing said sample and said first liquid test reagent system, respectively, in first and second cavities residing intermediate said capillary means upon said capillary means being in a rearward position and said reservoir; and
advancing said capillary means from said rearward position towards said reservoir to cause said capillary means to engage said liquid sample in said first cavity and draw said sample into said capillary means by capillary attraction, continuing advancement of said capillary means to cause said capillary means to engage said first liquid test reagent system residing in said second cavity to draw said first liquid test reagent system into said capillary means by capillary attraction and to bring said analyte and said first liquid test reagent system into contact in said capillary means and facilitate said reaction therebetween, and further continuing advancement of said capillary means to cause said capillary means to enter said reservoir through said entrance and engage said second liquid test reagent system to draw said second liquid test reagent system into said capillary means by capillary attraction and to bring said second liquid test reagent system and said admixture of said sample and said first liquid test reagent system into contact in said capillary means to facilitate said reaction therebetween.

45. The process according to claim 40 or 44 wherein said capillary means are a capillary tube, and wherein said process includes the further steps of providing said capillary tube with at least an optically transparent portion enabling optical determination of said reaction, mounting said capillary tube on mounting means and providing said mounting means with a magnifying portion for magnifying the view of said reaction in said capillary tube to enhance visual perception thereof by the human eye.

46. The process according to claim 44 wherein said process includes the further steps of and providing turbulent flow by capillary attraction respectively to said first and second liquid test reagent systems to bring said systems into turbulent contact in said capillary means respectively with said analyte and said admixture of said sample and said first liquid test reagent system to enhance facilitation of said reactions.

47. The process according to claim 44 wherein said capillary means comprise a capillary tube having a bore provided with a non-circular cross-section wherein said process includes the further steps of providing turbulent flow to said first liquid test reagent system by said capillary attraction and bringing said first liquid test reagent system into contact with said analyte in said capillary tube with capillary attraction driven turbulence generating a contact gradient therebetween increasing in the direction of turbulent flow to enhance facilitation of said reaction therebetween, and providing turbulent flow to said second liquid test reagent system by said capillary attraction and bringing said second liquid test reagent system into contact with said admixture of said sample and said first liquid test reagent system in said capillary tube with capillary attraction driven turbulence generating a contact gradient therebetween increasing in the direction of turbulent flow to enhance facilitation of said reaction therebetween.

48. The process according to claim 44 wherein said reservoir comprises capillary means and wherein said process includes the further step of placing said second liquid test reagent system in said capillary vessel by capillary attraction.

49. The process according to claim 44 wherein said reservoir comprises opposed, spaced apart members providing said reservoir therebetween and wherein said process includes the further step of placing said second liquid test reagent system in said reservoir by pipetting.

50. The process according to claim 44 wherein said process includes the further step of providing said capillary means with at least an optically transparent portion enabling optical determination of said reaction.

51. A process of facilitating reaction between analyte contained in a liquid sample and an analytical test reagent system and for providing a control test between said ample and a control test reagent system for comparison with said reaction to determine the validity thereof, comprising the steps of:
placing said analytical test reagent system in first capillary means;
placing said control test reagent system in second capillary means;
placing said liquid sample containing said analyte in a reservoir;
providing said first and second capillary means with cross-sectional dimensions permitting entry thereof into said reservoir;
mounting said first and second capillary means and said reservoir for at least relative movement towards each other and entry of said first and second capillary means into said reservoir; and
providing said relative movement and entry of said first and second capillary means into said reservoir and drawing by capillary attraction respective portions of said sample into said first capillary means and said second capillary means to bring said analyte and analytical test reagent system into contact in said first capillary means and facilitate said reaction and to bring a portion of said sample and said control test reagent system into contact in said second capillary means to provide said control test.

52. The process according to claim 51 wherein said process includes the further steps of providing turbulent flow by said capillary attraction to said portions of said sample to bring said portions of said sample respectively into turbulent contact in said first capillary means with said analytical test reagent system and in said second capillary means with said control test regent system.

53. The process according to claim 51 wherein said process includes the further steps of providing turbulent flow to said portions of said sample by said capillary attraction and bringing said portions of said sample respectively into contact with said analytical test reagent system in said first capillary means with capillary attraction driven turbulence generating a contact gradient therebetween increasing in the direction of turbulent flow to enhance facilitation of said reaction and into contact with said control test reagent system in said second capillary means with capillary attraction driven turbulence creating a gradient contact therebetween increasing in the direction of turbulent flow to enhance said control test.

54. The process according to claim 51 wherein said analytical and control test reagent systems are each a liquid and wherein said steps of placing said analytical and control test reagent systems in said first and second capillary means comprise the steps of drawing said analytical and control test reagent systems respectively into said first and second capillary means by capillary attraction.

55. The process according to claim 51 wherein said reservoir comprises capillary means and wherein the step of placing said sample in said reservoir means comprises the step of drawing said sample into said reservoir by capillary attraction.

56. The process according to claim 51 wherein said process includes the further step of providing each of said first and second capillary means with at least an optically transparent portion for enabling optical determination respectively of said reaction and said control test.

57. The process according to claim 51 wherein said first and second capillary means comprise first and second capillary tubes and wherein said process comprises the further steps of disposing said first and second capillary tubes substantially parallel, securing said first and second capillary tubes to a slide member mounted slidably on mounting means, advancing said slide member towards said reservoir means and advancing said first and second capillary tubes concurrently into said reservoir means.

58. The process according to claim 57 wherein said step of advancing said first and second capillary tubes concurrently into said reservoir means comprises the step of advancing said first and second capillary tube simultaneously into said reservoir means.

59. The process according to claim 57 wherein said process includes the further steps of providing each of said first and second capillary tubes with at least an optically transparent portion enabling optical determination respectively of said reaction and said control test and providing said mounting means with a magnifying portion for magnifying the views of said reaction and control test to enhance visual perception and comparison thereof by the human eye.

60. A process of facilitating reaction between analyte contained in a sample and test reagent system, at least one of said sample and test reagent system being a liquid, comprising the step of providing turbulent flow by capillary attraction through a bore of non-circular cross-section to said liquid one of said sample and test reagent system and turbulently flowing said liquid one into turbulent engagement with the other of said sample and test reagent system to bring said analyte and test reagent system into turbulent contact in said bore thereby facilitating said reaction.

61. A process of facilitating reaction between analyte contained in a sample and test reagent system, at least one of said sample and test reagent systems being a liquid, comprising the step of bringing said analyte and test reagent system into contact in a bore of non-circular cross-section with capillary attraction driven turbulence generating a contact gradient therebetween.

* * * * *